(12) United States Patent
Audonnet et al.

(10) Patent No.: US 6,586,412 B2
(45) Date of Patent: *Jul. 1, 2003

(54) POLYNUCLEOTIDE VACCINE FORMULA AGAINST CANINE PATHOLOGIES, IN PARTICULAR RESPIRATORY AND DIGESTIVE PATHOLOGIES

(75) Inventors: Jean-Christophe Audonnet, Lyons (FR); Annabelle Bouchardon, Lyons (FR); Michel Riviere, Ecully (FR)

(73) Assignee: Merial, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,982

(22) Filed: Feb. 16, 2001

(65) Prior Publication Data

US 2001/0009959 A1 Jul. 26, 2001

Related U.S. Application Data

(60) Division of application No. 09/232,477, filed on Jan. 15, 1999, now Pat. No. 6,228,846, which is a continuation-in-part of application No. PCT/FR97/01316, filed on Jul. 15, 1997.

(30) Foreign Application Priority Data

Jul. 19, 1996 (FR) ............................................ 96 09401

(51) Int. Cl.$^7$ ............................................... A61K 31/71
(52) U.S. Cl. ................... 514/44; 435/320.1; 536/23.72; 536/23.7
(58) Field of Search ........................ 514/44; 435/320.1; 536/23.72, 23.7

(56) References Cited

U.S. PATENT DOCUMENTS

| | | |
|---|---|---|
| 5,846,946 A | 12/1998 | Huebner et al. |
| 6,063,385 A | 5/2000 | Shultz |
| 6,187,759 B1 | 2/2001 | Tarpey et al. |
| 6,228,846 B1 * | 5/2001 | Audonnet et al. ............ 514/44 |

FOREIGN PATENT DOCUMENTS

| | | |
|---|---|---|
| FR | 2 010 678 A | 2/1970 |
| WO | WO 95/20660 | 8/1995 |
| WO | WO 97/40163 | 10/1997 |
| WO | WO 97/41236 | 11/1997 |

OTHER PUBLICATIONS

Schultz, J. et al. "Update on antiviral DNA vaccine research (1998–2000)." Interviology 2000 43:197–217.
Ertl, H.C., et al., "Plasmid Vectors as Anti–Viral Vaccines" DNA Vaccines, A New Era in Vaccinology Annals N.Y. Acad. Sci, 1995, vol. 6: 77–87.
Perrin, P., et al., "Immunization of Dogs with a DNA vaccine induces protection against rabies virus" Vaccine 2000, vol. 18: 479–486.
Osorio, J.E. et al "Immunization of dogs and cats with a DNA vaccine against rabies virus" Vaccine 1999, vol. 17: 1109–1116.
Z.Q. Xiang, et al., "Immune Response to Nucleic Acid Vaccines to Rabies Virus", Virology, vol. 209–2 (1995) pp. 569–579.
Jiang et al., Nucleic Acid Immunization Protects Dogs Against Challenge with Virulent Canine Parvorius, Vaccine 16(6):601–607, 1998.
Sixt et al., Canine Distemper Virus DNA Vaccination Induces Humoral and Cellular Immunity and Protects Against a Lethal Intracerebral Challenge, Journal of Virology, 72(11):8472–8476, 1998.
Tighe et al., Gene Vaccination: Plasmid DNA is More Than Just a Blueprint. Immunology Today 19(2):89097, 1998.

* cited by examiner

*Primary Examiner*—Donna Wortman
(74) *Attorney, Agent, or Firm*—Frommer Lawrence & Haug; William S. Frommer; Thomas J. Kowalski

(57) ABSTRACT

Disclosed is an immunological or vaccine composition that includes at least one plasmid that contains and expresses in vivo in host canine cells a nucleic acid molecule that encodes an antigen of a canine pathogen, such as rabies G. The plasmid can include more than one nucleic acid molecule such that the plasmid can express more than one antigen. Also disclosed are methods for using and kits employing such compositions.

20 Claims, 10 Drawing Sheets

FIG. 2

POLYNUCLEOTIDE VACCINE FORMULA AGAINST CANINE PATHOLOGIES, IN PARTICULAR RESPIRATORY AND DIGESTIVE PATHOLOGIES

This is a divisional of U.S. application Ser. No. 09/232,477, now U.S. Pat. No. 6,228,846, filed Jan. 15, 1999, which is a continuation-in-part of copending International Application PCT/FR97/01316 having an international filing date of Jul. 15, 1997, and designating the U.S. and claiming priority from French Application No. 96/09401, filed Jul. 19, 1996. Reference is also made to the applications of Audonnet et al., Ser. Nos. 09/232,278, 09/232,468, 09/232,279, 09/232,479 and 09/232,478, and to the application of Rijsewijk et al. Ser. No. 09/232,469, all filed Jan. 15, 1999. All of the above-mentioned applications, as well as all documents cited herein and documents referenced or cited in documents cited herein, are hereby incorporated herein by reference. Vectors of vaccines or immunological compositions of the aforementioned applications, as well as of documents cited herein or documents referenced or cited in documents cited herein or portions of such vectors (e.g., one or more or all of regulatory sequences such as DNA for promoter, leader for secretion, terminator), may to the extent practicable with respect to the preferred host of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors.

The present invention relates to a vaccine formula allowing the vaccination of dogs against a large number of infectious pathologies, in particular respiratory and digestive pathologies. It also relates to a corresponding method of vaccination.

Infectious dog pathology is extremely varied and often difficult to control depending on the circumstances encountered in the field.

A number of vaccines already exist, in particular against Carré's disease (CDV virus), parvovirosis (CPV virus), coronavirosis (CCV virus) kennel cough or respiratory complex (PI2 virus) and rabies (rhabdovirus). These vaccines are, more generally, live vaccines consisting of attenuated strains. This is especially the case for Carré's disease vaccines, vaccines against canine adenoviroses, vaccines against parvovirosis and vaccines against the canine coronavirus.

In some cases, inactivated vaccines have also been proposed, as for rabies and coronavirosis.

These various vaccines are sold either separately, that is to say in the form of monovalent vaccines, or in the form of associated, that is to say polyvalent, vaccines.

The polyvalent associations developed up until now have always posed problems of compatibility between the valencies and of stability. It is indeed necessary to ensure at the same time the compatibility between the different valencies of the vaccine, whether from the point of view of the different antigens used or from the point of view of the formulations themselves, especially in the case where both inactivated vaccines and live vaccines are combined. It also poses the problem of preservation of such combined vaccines and also of their safety especially in the presence of adjuvant. These vaccines are in general quite expensive.

The degree of protection and the duration of this protection can, in addition, be highly variable and are also sensitive to the circumstances in the field. This is particularly true of the vaccination of puppies, in which the antibodies of maternal origin prevent immunization by the inactivated vaccines and even by live vaccines.

It may therefore be desirable to perfect the vaccination of Canidae, and especially dogs, while keeping in mind the economic constraints acting against the use of vaccines which are expensive or complicated to use.

Vaccination trials against Carré's disease using purified preparations of F fusion antigens and of H haemaglutinin equivalents in complete Freund's adjuvant have suggested that the F antigen might constitute an immunogen of interest for protection against the CDV virus (E. Norrby et al., J. of Virol. May 1986: 536–541) for a subunit vaccine.

Another article (P. de Vries et al., J. gen. Virol. 1988, 69: 2071–2083) suggests, on the other hand, that the CDV F and HA proteins might be advantageous in a vaccination according to the technique of immunostimulatory complexes (ISCOMS).

Mice immunized with a recombinant vaccine expressing the gene for the CDV F protein were protected against challenge with this virus.

These are, however, laboratory results, which are difficult to interprete especially under field conditions.

As regards parvoviroses, trials of subunit vaccines containing the major capsid protein VP2 from the CPV virus obtained by genetic recombination in the baculovirus made it possible to show protection of dogs thus immunized against challenge with the CPV virus.

As regards the canine herpesvirus CHV, studies have been carried out on the use of glycoproteins as components of subunit vaccines. These studies have shown the induction of cross-responses with other herpesviruses such as FHV but do not draw any conclusion on the possibilities of making a protective vaccine.

For the Lyme disease, associated OspA and OspB induce protection in mice and dogs and OspA alone in mice, hamsters and dogs.

Patent applications WO-A-90 11092, WO-A-93 19183, WO-A-94 21797 and WO-A-95 20660 have made use of the recently developed technique of polynucleotide vaccines. It is known that these vaccines use a plasmid capable of expressing, in the host cells, the antigen inserted into the plasmid. All routes of administration have been proposed (intraperitoneal, intravenous, intramuscular, transcutaneous, intradermal, mucosal and the like). Various means of vaccination can also be used, such as DNA deposited at the surface of gold particles and projected so as to penetrate into the animal's skin (Tang et al., Nature 356, 152–154, 1992) and liquid jet injectors which make it possible to transfect the skin, muscle, fatty tissues as well as the mammary tissues (Furth et al., Analytical Biochemistry, 205, 365–368, 1992). (See also U.S. Pat. Nos. 5,846,946, 5,620,896, 5,643,578, 5,580,589, 5,589,466, 5,693,622, and 5,703,055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8):801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.)

The polynucleotide vaccines may use both naked DNAs and DNAs formulated, for example, inside liposomes or cationic lipids.

The prior art, on the other hand, gives no result of protection in dogs by the polynucleotide method of vaccination against these diseases. Much less is yet known about the canine coronavirus CCV and about the agents responsible for the respiratory complex.

As regards rabies, protection of mice against virulent challenge has been demonstrated after treatment with a polynucleotide vaccine expressing the gene for the G protein under the control of the SV40 virus early promoter (Xiang et al., Virology 199, 1994: 132–140), a similar result being achieved by using the CMV IE promoter.

The invention proposes to provide a multivalent vaccine formula which makes it possible to ensure vaccination of dogs against a number of pathogenic agents.

Another objective of the invention is to provide such a vaccine formula combining different valencies while exhibiting all the required criteria of mutual compatibility and stability of the valencies.

Another objective of the invention is to provide such a vaccine formula which makes it possible to combine different valencies in the same vehicle.

Another objective of the invention is to provide such a vaccine formula which is easy and inexpensive to use.

Yet another objective of the invention is to provide a method of vaccination which makes it possible to considerably increase the efficacy of the vaccine according to the invention or to substantially reduce the quantity of vaccine necessary, and having good safety.

The subject of the present invention is therefore a vaccine formula against Canidae pathogens, comprising at least two vaccine valencies each comprising a plasmid integrating, so as to express it in vivo in the Canidae cells, a gene with one canine pathogen valency, namely a Carré's disease virus CDV valency and a canine parvovirus CPV valency, the plasmids comprising, for each valency, one or more of the genes selected from the group consisting of HA and F for the Carré's disease virus and the VP2 gene for the canine parvovirus.

Preferably, for the Carré's disease valency, the plasmid (s) comprise the HA and F genes, either inserted into the same plasmid, or inserted into different plasmids.

The multivalent vaccine according to the invention may also comprise a canine coronavirus CCV valency, with one or several plasmids comprising one or more of the genes selected from the group of the S and M genes and preferably the S gene or the S and M genes. Here also, the genes may be inserted into different plasmids or grouped together in the same plasmid in a context allowing their expression. The abovementioned bi- or trivalent vaccine according to the invention may also comprise, in addition, a valency effective for the prevention of the respiratory complex, namely a PI2 valency comprising one or several plasmids which comprise at least one of the HA and F genes. Preferably, the use of both the two HA and F genes is envisaged.

Other advantageous valencies in the case of the present invention may therefore be associated with the vaccines according to the invention, namely one or more of the valencies selected from the group formed by the herpesvirosis CHV, Lyme disease and rabies, the plasmids comprising, for each valency, one or more of the genes selected from the group composed of the gB and gD genes for the CHV virus, the OspA, OspB and p100 genes for *B. burgdorferi* (Lyme disease), and the G gene for rabies.

Preferably, for herpesvirosis, the two gB and gD genes are associated either in two separate plasmids, or in a single plasmid. For Lyme disease, the OspA gene is preferred.

Preferably, the vaccine according to the invention comprising the Carré's disease and parvovirosis valencies will comprise, as other valency, the coronavirosis valency or, less preferably, the respiratory complex valency, or these two valencies, it being understood that any combination comprising, one, several or all the coronavirosis, respiratory complex, herpesvirosis, Lyme disease and rabies valencies can be associated with the two Carré's disease and parvovirosis valencies.

Valency in the present invention is understood to mean at least one antigen providing protection against the virus for the pathogen considered, it being possible for the valency to contain, as subvalency, one or more modified or natural genes from one or more strains of the pathogen considered.

Pathogenic agent gene is understood to mean not only the complete gene but also the various nucleotide sequences, including fragments which retain the capacity to induce a protective response. The notion of the gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

The different valencies are contained in the vaccinal formulation according to the invention in a therapeutically effective quantity.

Preferably, the vaccine formula according to the invention can be provided in a suitable vehicle for administration, preferably by the intramuscular route, in a dose volume of between 0.1 and 5 ml, preferably between 0.5 and 2 ml.

The dose will be generally between 10 ng and 1 mg, preferably 100 ng and 500 $\mu$g, and preferably between 1 $\mu$g and 250 $\mu$g per plasmid type.

Use will preferably be made of naked plasmids simply placed in the vaccination vehicle which will be in general physiological saline (0.9% NaCl), ultrapure water, TE buffer and the like. All the polynucleotide vaccine forms described in the prior art can of course be used.

Each plasmid comprises a promoter capable of ensuring the expression of the gene inserted, under its control, into the host cells. This will be in general a strong eukaryotic promoter and in particular a cytomegalovirus early CMV-IE promoter of human or murine origin, or optionally of another origin such as rats, pigs and guinea pigs.

More generally, the promoter may be either of viral origin or of cellular origin. As viral promoter other than CMV-IE, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, such as for example the desmin promoter (Bolmont et al., Journal of Submicroscopic Cytology and Pathology, 1990, 22, 117–122; and Zhenlin et al., Gene, 1989, 78, 243–254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen (s) of each valency, but it is also possible to envisage causing antigens of several valencies to be expressed by the same plasmid.

The subject of the present invention is also a method for vaccinating dogs, comprising the administration of an effective dose of a vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered in the context of this method of vaccination, by the different routes of administration proposed in the prior art in the case of polynucleotide vaccination and by means of known techniques of administration, the preferred route being the intramuscular route.

The efficiency of presentation of the antigens to the immune system varies according to the tissues. In particular, the mucous membranes of the respiratory tree serve as barrier to the entry of pathogens and are associated with lymphoid tissues which support local immunity. The administration of a vaccine by contact with the mucous membranes, in particular the buccal mucous membrane, the pharyngeal mucous membrane and the mucous membrane of the bronchial region, is certainly of interest for vaccination against respiratory and digestive pathologies.

Consequently, the mucosal routes of administration form part of a mode of administration for the invention using in particular nebulization or spray or drinking water. It will be possible to apply the vaccine formulae and the vaccination methods according to the invention in this content.

The subject of the invention is also monovalent vaccine formulae comprising one or more plasmids encoding one or more genes from one of the viruses above, the genes being those described above. Besides their monovalent character, these formulae may possess the characteristics stated above as regards the choice of the genes, their combinations, the composition of the plasmids, the dose volumes, the doses and the like.

The monovalent vaccine formulae may be used (i) for the preparation of a polyvalent vaccine formula as described above, (ii) individually against the actual pathology, (iii) combined with a vaccine of another type (live or inactivated whole, recombinant, subunit) against another pathology, or (iv) as booster for a vaccine as described below.

The subject of the present invention is in fact also the use of one or more plasmids according to the invention for the manufacture of a canine vaccine intended to vaccinate animals first vaccinated by means of a first conventional vaccine (monovalent or multivalent) of the type in the prior art, in particular selected from the group consisting of a live whole vaccine, an inactivated whole vaccine, a subunit vaccine, a recombinant vaccine, this first vaccine having (that is to say containing or capable of expressing) the antigen(s) encoded by the plasmid(s) or antigen(s) providing cross-protection.

Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also the method of vaccination consisting in making a first vaccination as described above and a booster with a vaccine formula according to the invention.

In a preferred embodiment of the process according to the invention, there is administered in a first instance, to the animal, an effective dose of the vaccine of the conventional, especially inactivated, live, attenuated or recombinant type, or alternatively a subunit vaccine, so as to provide a first vaccination, and, after a period preferably of 2 to 6 weeks, the polyvalent or monovalent vaccine according to the invention is administered.

The subject of the invention is also a vaccination kit grouping together a first-vaccination vaccine as described above and a vaccine formula according to the invention for the booster. It also relates to a vaccine formula according to the invention accompanied by a leaflet indicating the use of this formula as a booster for a first vaccination as described above.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

BRIEF DESCRIPTION OF THE DRAWINGS

FIG. 2: Plasmid pAB044

Figure 1:
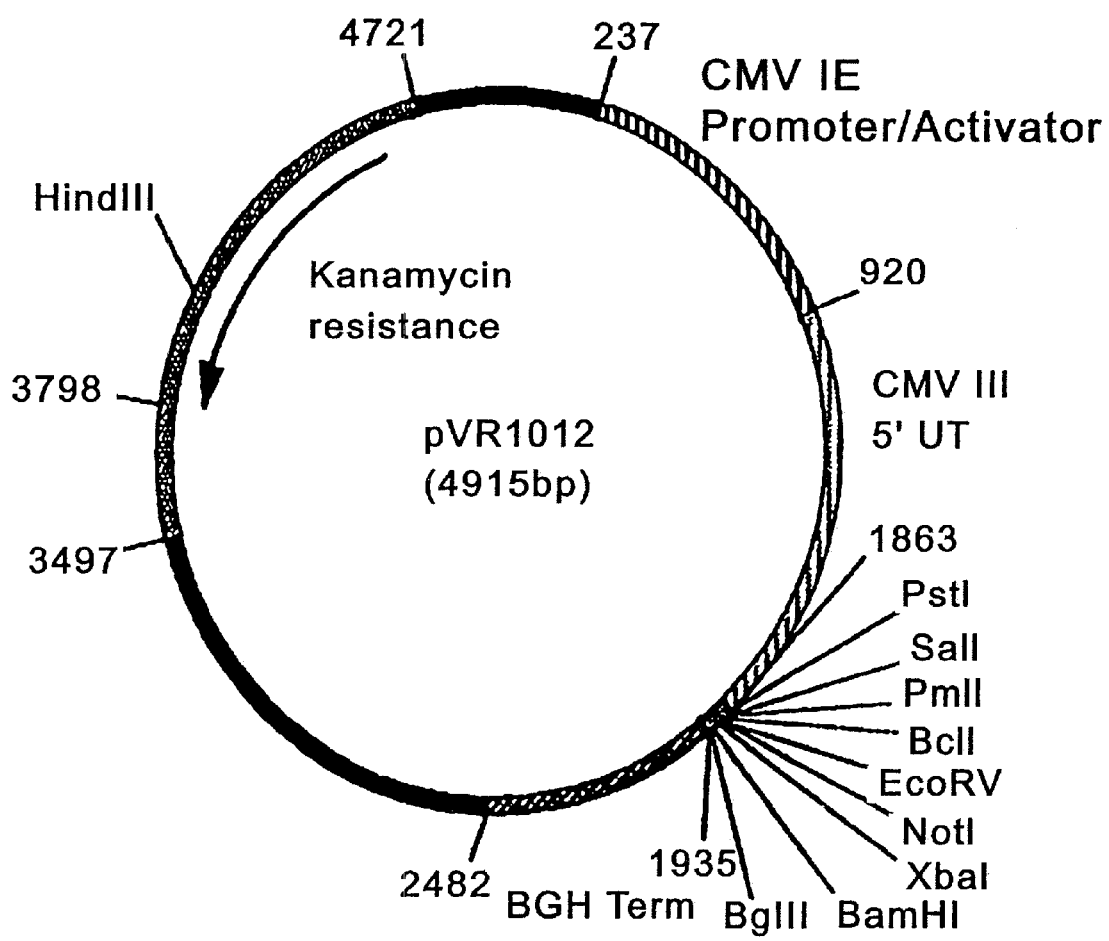
FIG. 1: Plasmid pVR1012

SEQUENCE LISTING SEQ ID NO.

SEQ ID No. 1: oligonucleotide AB017
SEQ ID No. 2: Oligonucleotide AB018
SEQ ID No. 3: Oligonucleotide AB085
SEQ ID No. 4: Oligonucleotide AB086
SEQ ID No. 5: oligonucleotide AB053
SEQ ID No. 6: Oligonucleotide AB054
SEQ ID No. 7: Oligonucleotide AB045
SEQ ID No. 8: Oligonucleotide AB048
SEQ ID No. 9: Oligonucleotide AB049
SEQ ID No. 10: Oligonucleotide AB050
SEQ ID No. 11: Oligonucleotide AB087
SEQ ID No. 12: Oligonucleotide AB088
SEQ ID No. 13: Oligonucleotide AB089
SEQ ID No. 14: Oligonucleotide AB090
SEQ ID No. 15: Oligonucleotide AB038
SEQ ID No. 16: Oligonucleotide AB039
SEQ ID No. 17: Oligonucleotide AB011
SEQ ID No. 18: Oligonucleotide AB012

EXAMPLES

Example 1

Culture of the Viruses

The viruses are cultured on the appropriate cellular system until a cytopathic effect is obtained. The cellular systems to be used for each virus are well known to persons skilled in the art. Briefly, cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

Example 2

Culture of the Bacteria

The *Borrelia burgdorferi* strains are cultured in appropriate media and according to conditions well known to persons skilled in the art. These conditions and media are in particular described by A. Barbour (J. Biol. Med. 1984, 57, 71–75). The extraction of the bacterial DNA was carried out according to the conditions described by W. Simpson et al. (Infect. Immun. 1990, 58, 847–853). The usual techniques described by J. Sambrook et al. (*Molecular Cloning: A Laboratory Manual*, 2nd Edition, Cold Spring Harbor Laboratory, Cold Spring Harbor, N.Y., 1989) can also be used.

Example 3

Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 µg/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultrapure water. It can then be digested with restriction enzymes.

Example 4

Isolation of the Viral Genomic RNAs

The RNA viruses were purified according to techniques well known to persons skilled in the art. The genomic viral RNA of each virus was then isolated using the "guanidium thiocyanate/phenol-chloroform" extraction technique described by P. Chomczynski and N. Sacchi (Anal. Biochem., 1987, 162, 156–159).

Example 5

Molecular Biology Techniques

All the constructions of plasmids were carried out using the standard molecular biology techniques described by J. Sambrook et al. (*Molecular Cloning:* A Laboratory Manual, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 6

RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (Sambrook J. et al., 1989). Each RT-PCR reaction was performed with a pair of specific amplimers and taking, as template, the viral genomic RNA extracted. The complementary DNA amplified was extracted with phenol/chloroform/isoamyl alcohol (25:24:1) before being digested with restriction enzymes.

Example 7

Plasmid pVR1012

The plasmid pVR1012 (FIG. 1) was obtained from Vical Inc., San Diego, Calif., USA. Its construction has been described in J. Hartikka et al. (Human Gene Therapy, 1996, 7, 1205–1217).

Example 8

Construction of the Plasmid pAB044 (CDV HA gene)

Figure 2:
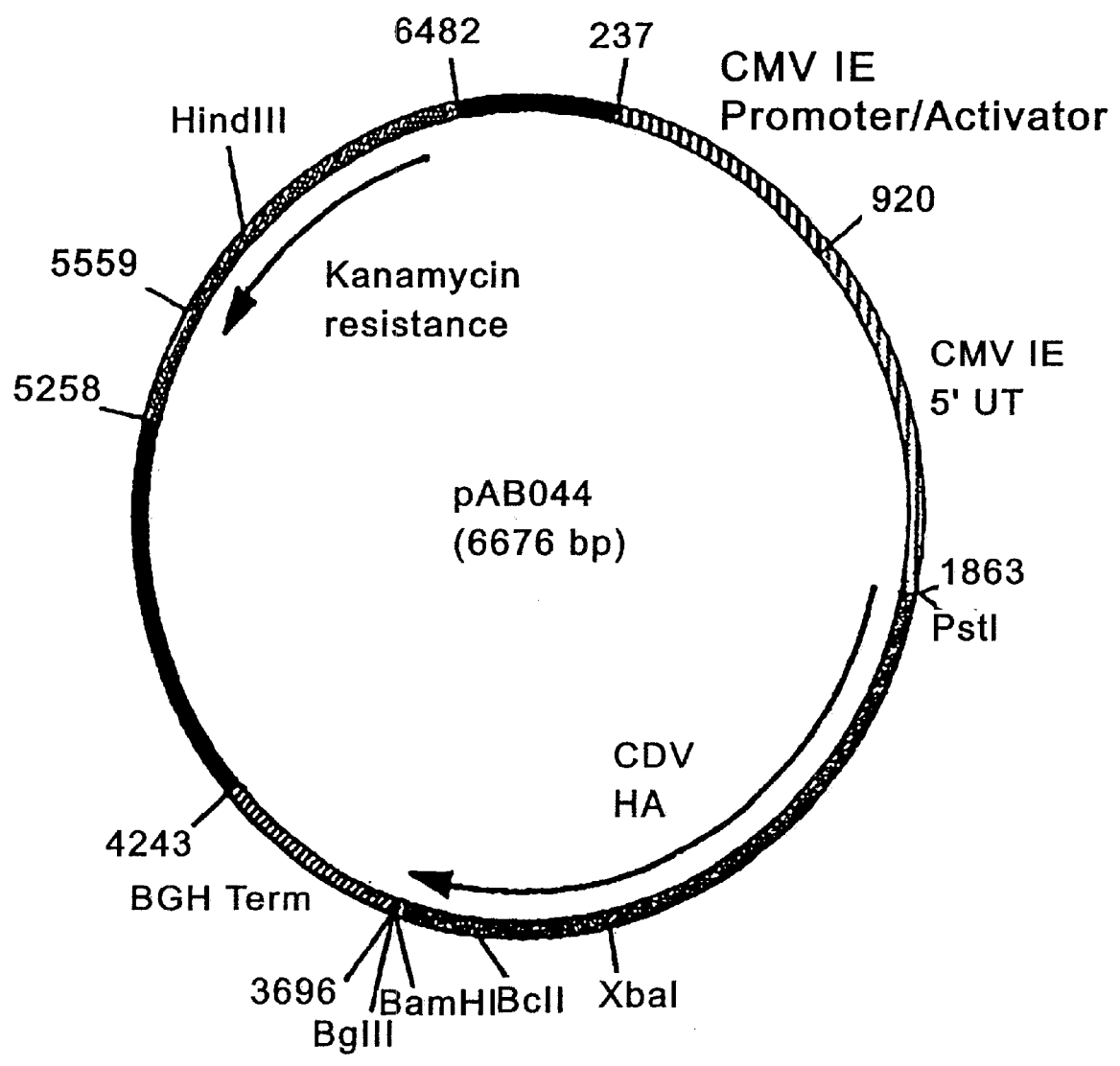

An RT-PCR reaction according to the technique of Example 6 was carried out with the Carré's disease virus (CDV) (Onderstepoort strain) genomic RNA (M. Sidhu et al., Virology, 1993, 193, 66–72), prepared according to the technique of Example 4, and with the following oligonucleotides:
AB017 (35 mer) (SEQ ID No. 1)
5' AAAACTGCAGAATGCTCCCCTACCAAGA-CAAGGTG 3'
AB018 (37 mer) (SEQ ID No. 2)
5'           CGCGGATCCTTAACGGTTACAT-GAGAATCTTATACGG 3'
so as to isolate the gene encoding the CDV HA glycoprotein in the form of a PstI-BamHI fragment. After purification, the 1835 bp RT-PCR product was digested with PstI and BamHI in order to isolate a 1817 bp PstI-BamHI fragment. This fragment was ligated with the vector pVR1012 (Example 7) previously digested with PstI and BamHI, to give the plasmid pAB044 (6676 bp (FIG. 2).

Example 9

Construction of the Plasmid pAB036 (CDV F Gene)

Figure 3:
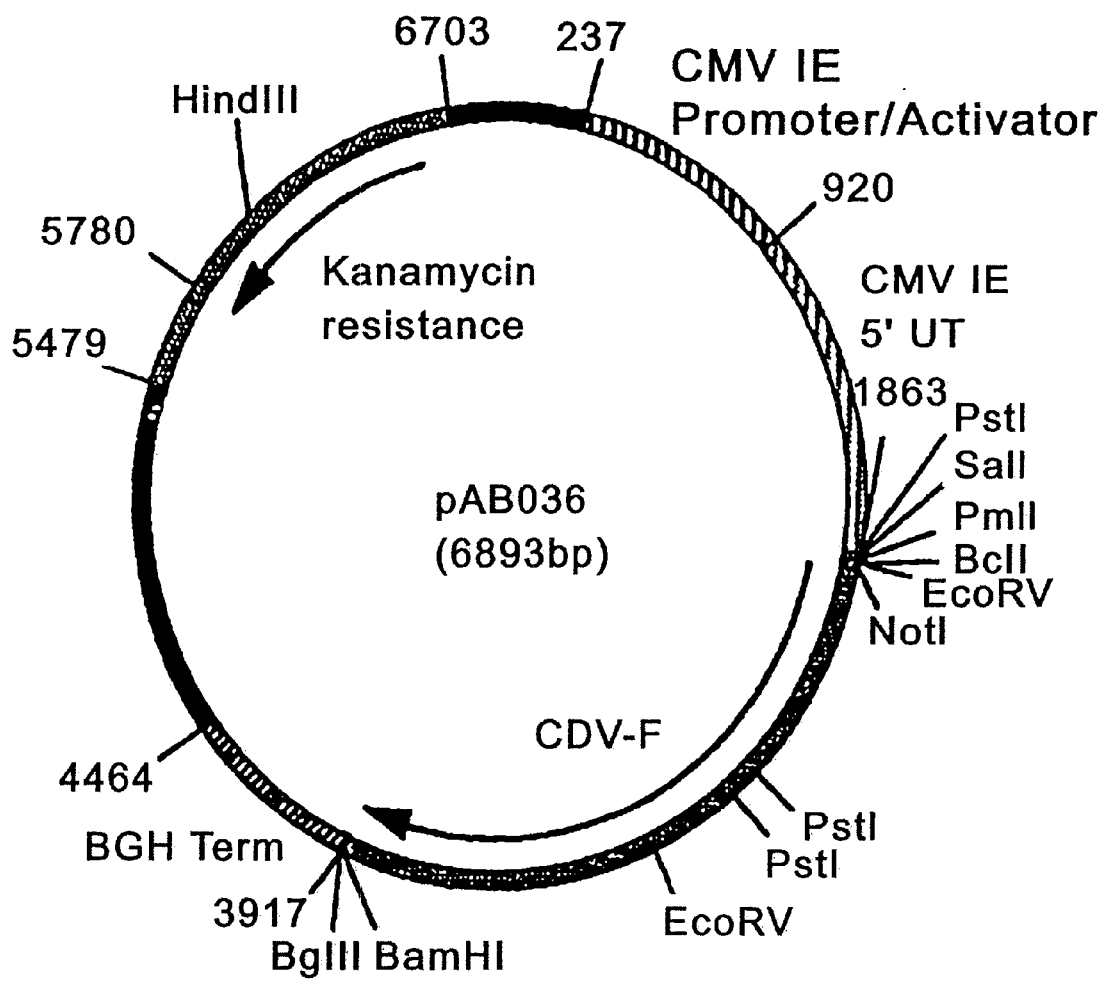
FIG. 3: Plasmid pAB036

An RT-PCR reaction according to the technique of Example 6 was carried out with the Carré's disease virus (CDV) (Onderstepoort strain) genomic RNA (R. Driellen, Genbank sequence accession No.=X65509), prepared according to the technique of Example 4, and with the following oligonucleotides:
AB085 (40 mer) (SEQ ID No. 3)
5' ATAAGAAGCGGCCGCACATGCACAAGG-GAATCCCCAAAAG 3'
AB086 (32 mer) (SEQ ID No. 4)
5' CGCGGATCCACTTCAGTGTGATCTCACATAGG 3'
so as to isolate the gene encoding the CDV F glycoprotein in the form of an NotI-BamHI fragment. After purification, the 2018 bp RT-PCR product was digested with NotI and BamHI in order to isolate a 2000 bp NotI-BamHI fragment. This fragment was ligated with the vector pVR1012 (Example 7), previously digested with NotI and BamHI, to give the plasmid pAB036 (6893 bp) (FIG. 3).

Example 10

Construction of the Plasmid pAB024 (Canine Parvovirus VP2 Gene)

Figure 4:
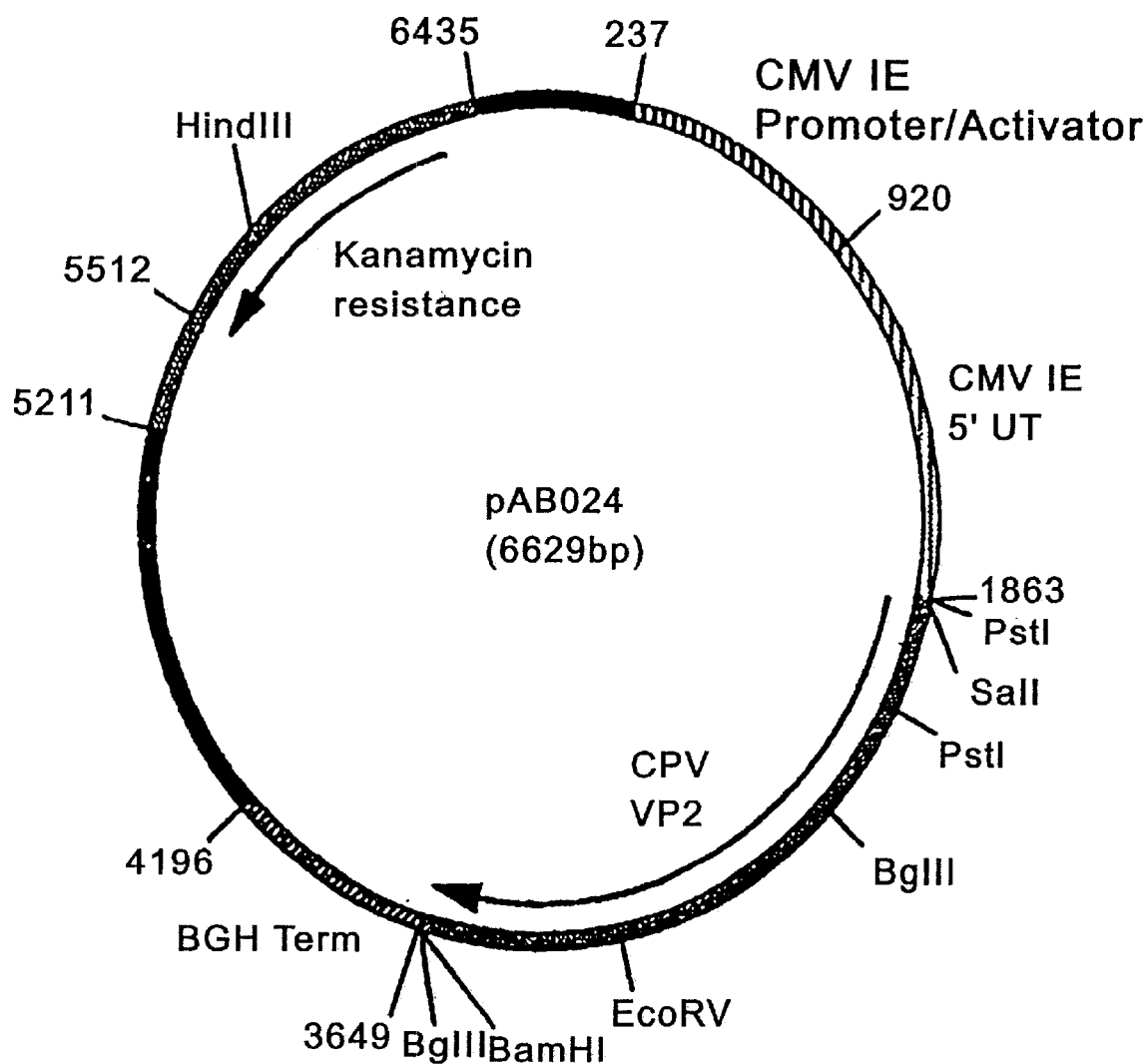
FIG. 4: Plasmid pAB024

A PCR reaction was carried out with the canine parvovirus (CPV) (CPV-b strain) genomic DNA (C. Parrish Genbank sequence accession No.=M19296), prepared according to the technique of Example 3, and with the following oligonucleotides:
AB053 (33 mer) (SEQ ID No. 5)
5' ACGCGTCGACATGAGTGATGGAGCAGTTCAACC 3'
AB054 (33 mer) (SEQ ID No. 6)
5' CGCGGATCCTTAATATAATTTTCTAGGTGCTAG 3'
so as isolate the gene encoding the VP2 capsid protein (CPV VP2) in the form of a SalI-BamHI fragment. After purification, the 1773 bp PCR product was digested with SalI and BamHI in order to isolate a 1760 bp SalI-BamHI fragment. This fragment was ligated with the vector pVR1012 (Example 7), previously digested with SalI and BamHI, to give the plasmid pAB024 (6629 bp) (FIG. 4).

Example 11

Construction of the Plasmid pAB021 (CCV S Gene)

Figure 5:
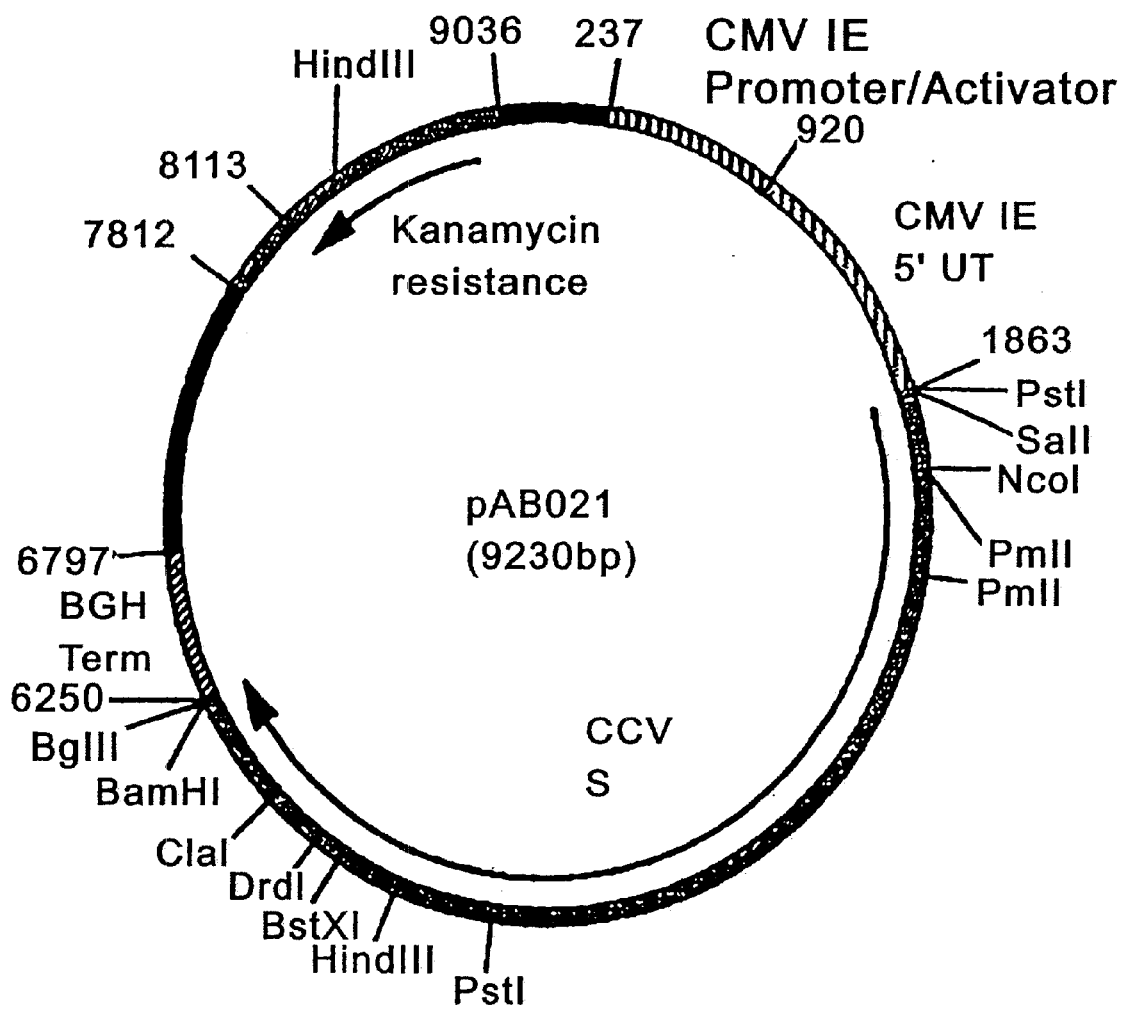
FIG. 5: Plasmid pAB021

An RT-PCR reaction according to the technique of Example 6 was carried out with the canine coronavirus (CCV) genomic RNA (B. Horsburgh et al., J. Gen. Virol. 1992, 73, 2849–2862), prepared according to the technique of Example 4, and with the following oligonucleotides:
AB045 (32 mer) (SEQ ID No. 7)
5' ACGCGTCGACATGATTGTGCTTACATTGTGCC 3'
AB048 (35 mer) (SEQ ID No. 8)
5' CGCGGATCCTCAGTGAACAT-GAACTTTTTCAATAG 3'
so as to amplify a 4374 bp fragment containing the gene encoding the CCV S glycoprotein in the form of a SalI-BamHI fragment. After purification, the RT-PCR product was digested with SalI and BamHI to give a 4361 bp SalI-BamHI fragment.
This fragment was ligated with the vector pVR1012 (Example 7), previously digested with SalI and BamHI to give the plasmid pAB021 (9230 bp) (FIG. 5).

Example 12

Construction of the Plasmid pAB022 (CCV M Gene)

Figure 6:
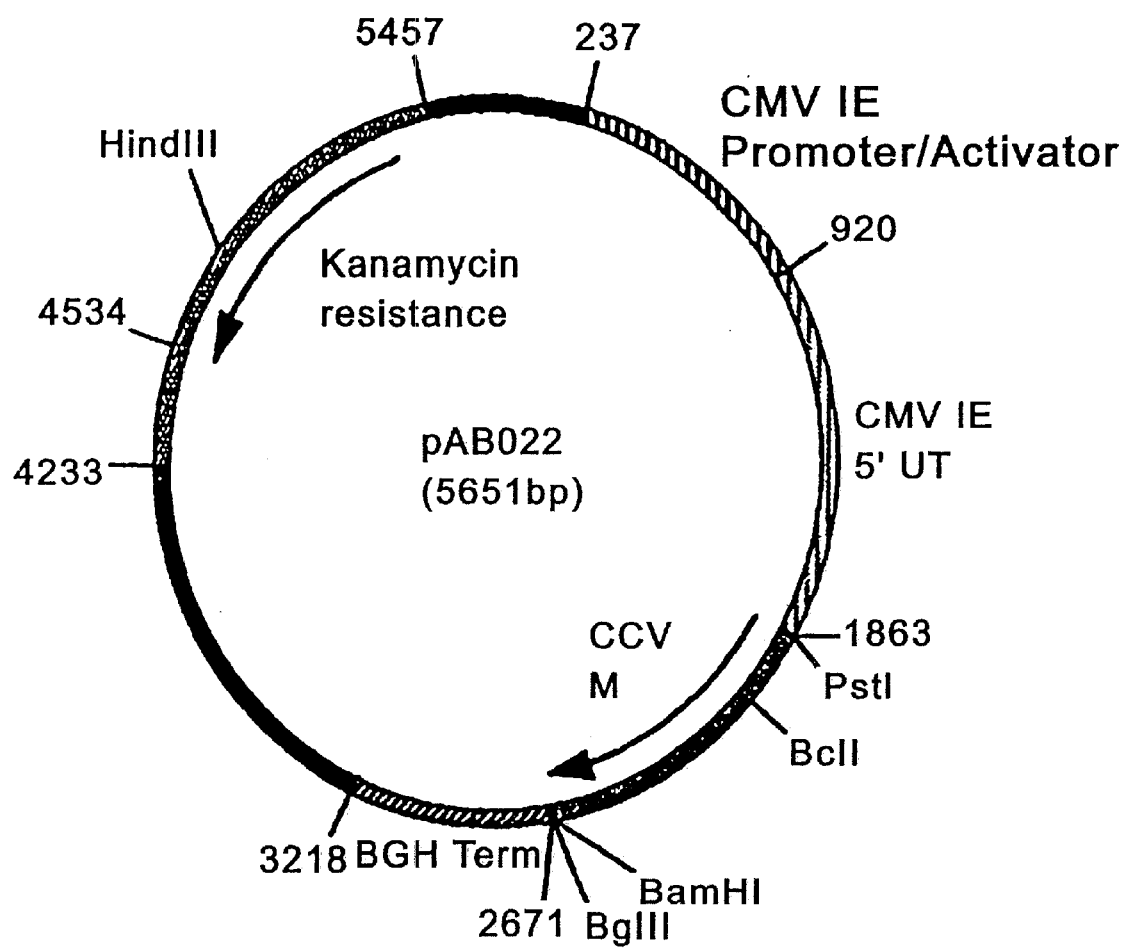
FIG. 6: Plasmid pAB022

An RT-PCR reaction according to the technique of Example 6 was carried out with the canine coronavirus (CCV) genomic RNA (B. Horsburgh et al., J. Gen. Virol. 1992, 73, 2849–2862), prepared according to the technique of Example 4, and with the following oligonucleotides:
AB049 (34 mer) (SEQ ID No. 9)
5' AAAACTGCAGAAATGAAGAAAATTTTGTTTTAC 3'
AB050 (33 mer) (SEQ ID No. 10)
5' CGCGGATCCTTATACCATATGTAATAATTTTC 3'
so as to isolate the gene encoding the M glycoprotein (CCV M) in the form of a PstI-BamHI fragment. After purification, the 809 bp RT-PCR product was digested with PstI and BamHI in order to isolate a 792 bp PstI-BamHI fragment. This fragment was ligated with the vector pVR1012 (Example 7), previously digested with PstI and BamHI, to give the plasmid pAB022 (5651 bp) (FIG. 6).

Example 13

Construction of the Plasmid pAB037 (CHV gB Gene)

Figure 7:
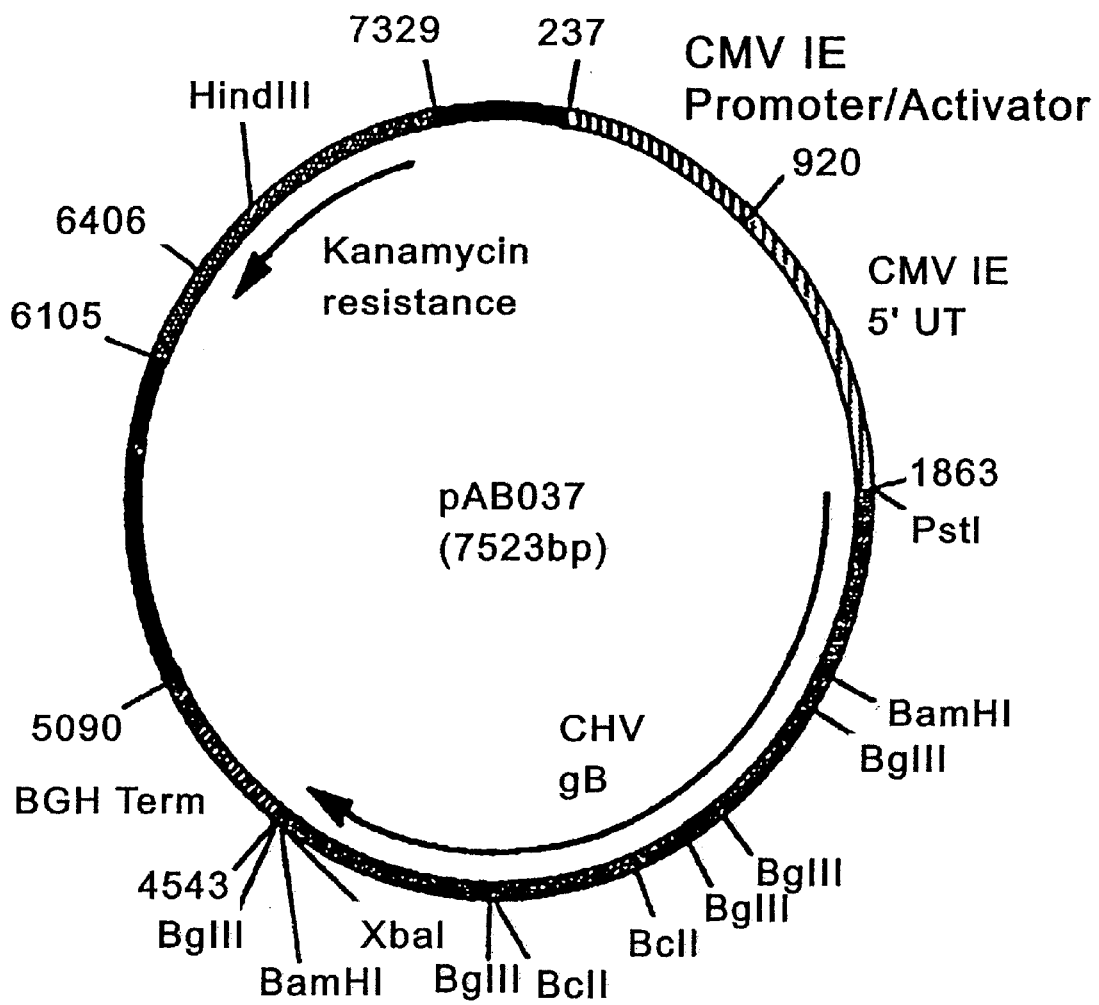
FIG. 7: Plasmid pAB037

A PCR reaction was carried out with the canine herpesvirus (CHV) (Carmichael strain) genomic DNA (K. Limbach et al., J. Gen. Virol. 1994, 75, 2029–2039), prepared according to the technique of Example 3, and with the following oligonucleotides:
AB087 (34 mer) (SEQ ID No. 11)
5' AAAACTGCAGAAGTATGTTTTCATTGTATCTATA 3'
AB088 (34 mer) (SEQ ID No. 12)
5' CTAGTCTAGATTATTAAACTTTACTTTCATTTTC 3'
so as to isolate the gene encoding the CHV virus gB glycoprotein in the form of a PstI-XbaI fragment. After purification, the 2667 bp PCR product was digested with PstI and XbaI in order to isolate a 2648 bp PstI-XbaI fragment. This fragment was ligated with the vector pVR1012 (Example 7), previously digested with PstI-XbaI, to give the plasmid pAB037 (7523 bp) (FIG. 7).

Example 14

Construction of the Plasmid pAB038 (CHV gD Gene)

Figure 8:
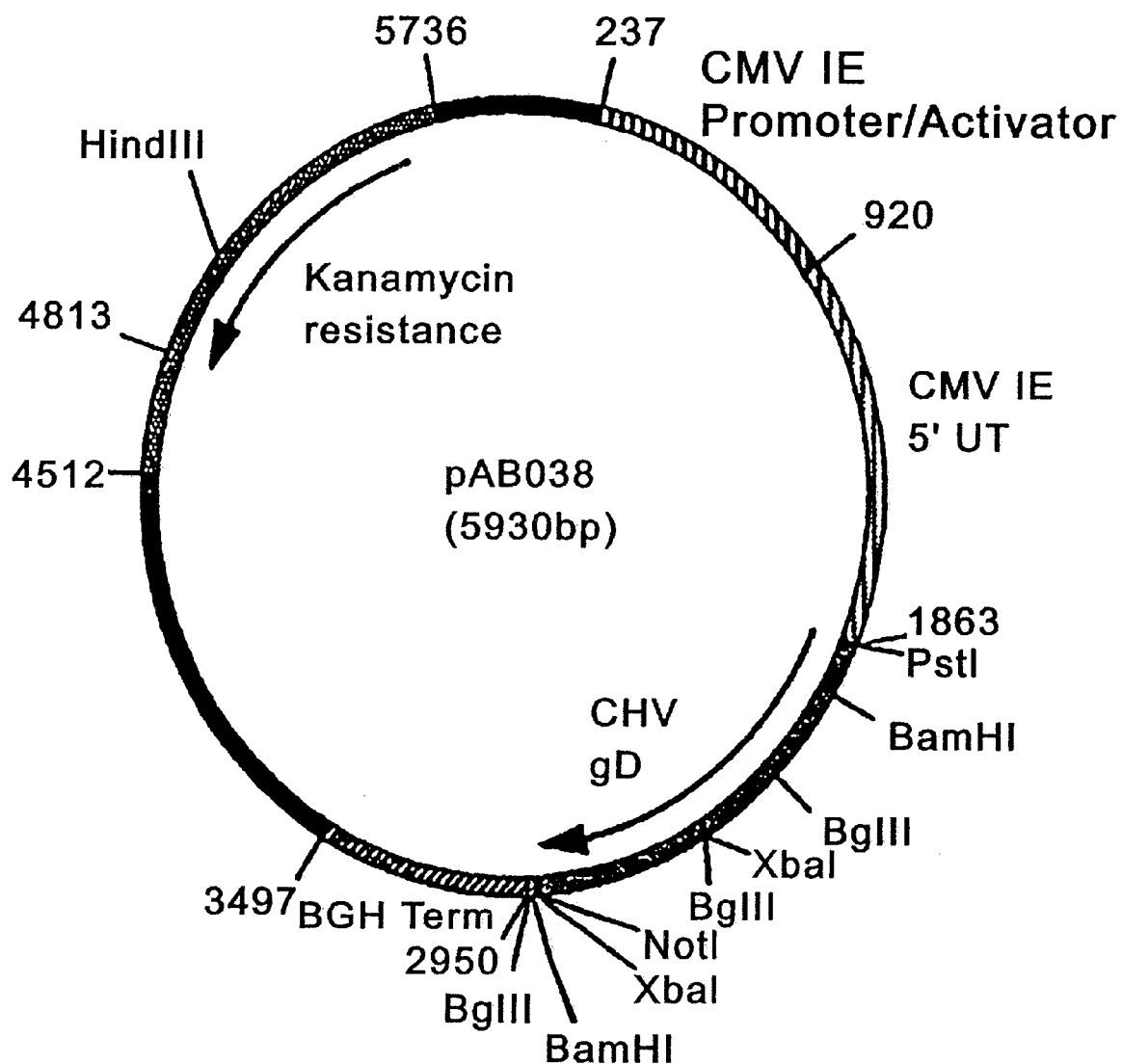
FIG. 8: Plasmid pAB038

A PCR reaction was carried out with the canine herpesvirus (CHV) (Carmichael strain) genomic DNA (K. Limbach et al., J. Gen. Virol. 1994, 75, 2029–2039), prepared according to the technique of Example 3, and with the following oligonucleotides:
AB089 (34 mer) (SEQ ID No. 13)
5' AAAACTGCAGAAAATGATTAAACTTCTATTTATC 3'
AB090 (35 mer) (SEQ ID No. 14)
5' ATAAGAATGCGGCCGCAAAGGCTAAA-CATTTGTTG 3'
so as to isolate the gene encoding the CHV virus gD glycoprotein in the form of a PstI-NotI fragment. After purification, the 1072 bp PCR product was digested with PstI and NotI in order to isolate a 1049 bp PstI-NotI fragment. This fragment was ligated with the vector pVR1012 (Example 7), previously digested with PstI and NotI, to give the plasmid pAB038 (5930 bp) (FIG. 8).

Example 15

Construction of the Plasmid pAB017 (*Borrelia burgdorferi* ospA Gene)

Figure 9:
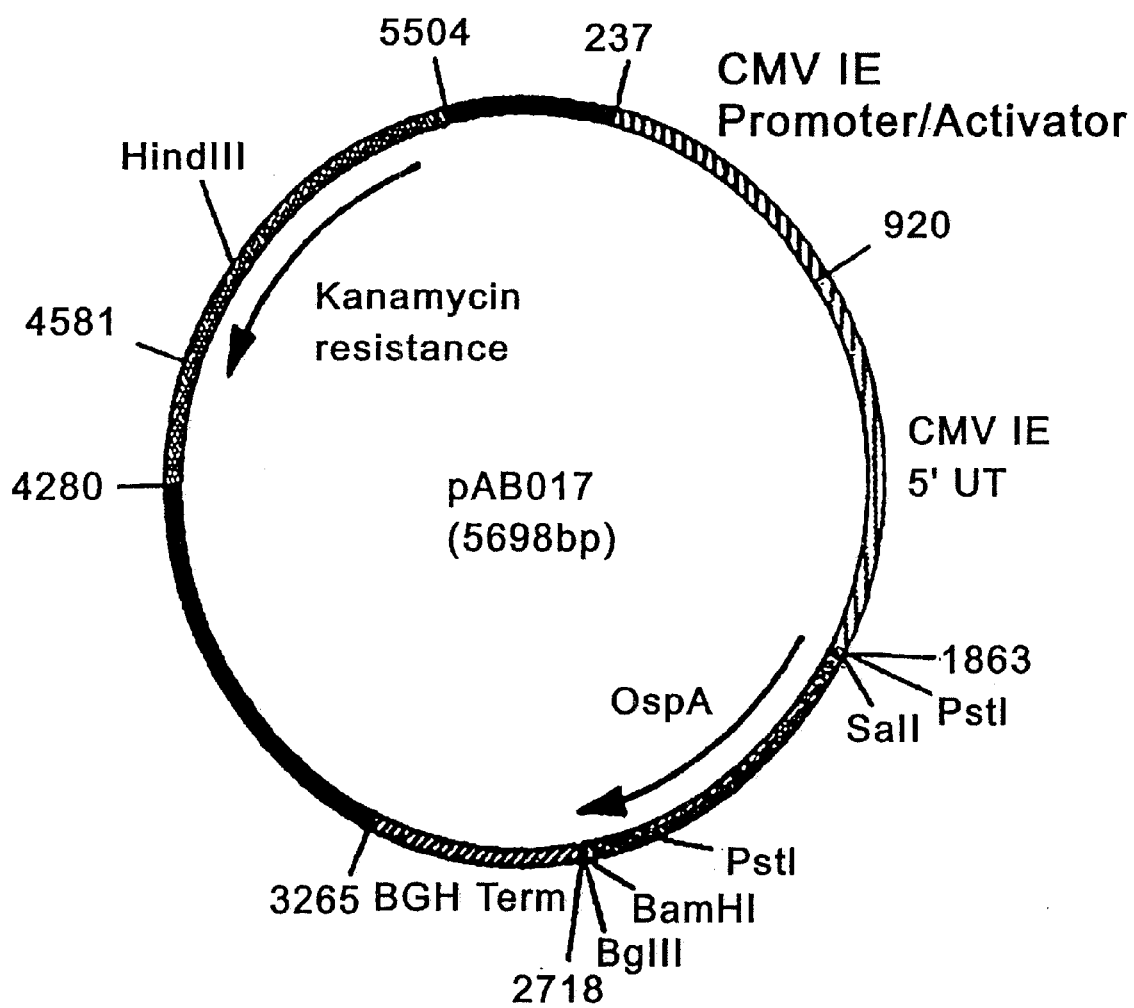
FIG. 9: Plasmid pAB017

A PCR reaction was carried out with the *Borrelia burgdorferi* (B31 strain) genomic DNA (S. Bergstrom et al., Mol. Microbiol. 1989, 3, 479–486), prepared according to the technique of Example 2, and with the following oligonucleotides:
AB038 (37 mer) (SEQ ID No. 15)
5' ACGCGTCGACTATGAAAAAATATTTAT-TGGGAATAGG 3'
AB039 (34 mer) (SEQ ID No. 16)
5' CGCGGATCCCTTATTTTAAAGCGTTTTTAATTTC 3'
so as to isolate the gene encoding the OspA membrane protein in the form of a SalI-BamHI fragment. After purification, the 842 bp PCR product was digested with SalI and BamHI in order to isolate an 829 bp SalI-BamHI fragment. This fragment was ligated with the vector pVR1012 (Example 7), previously digested with SalI and BamHI, to give the plasmid pAB017 (5698 bp) (FIG. 9).

Example 16

Construction of the Plasmid pAB041 (rabies Virus G Gene)

Figure 10:
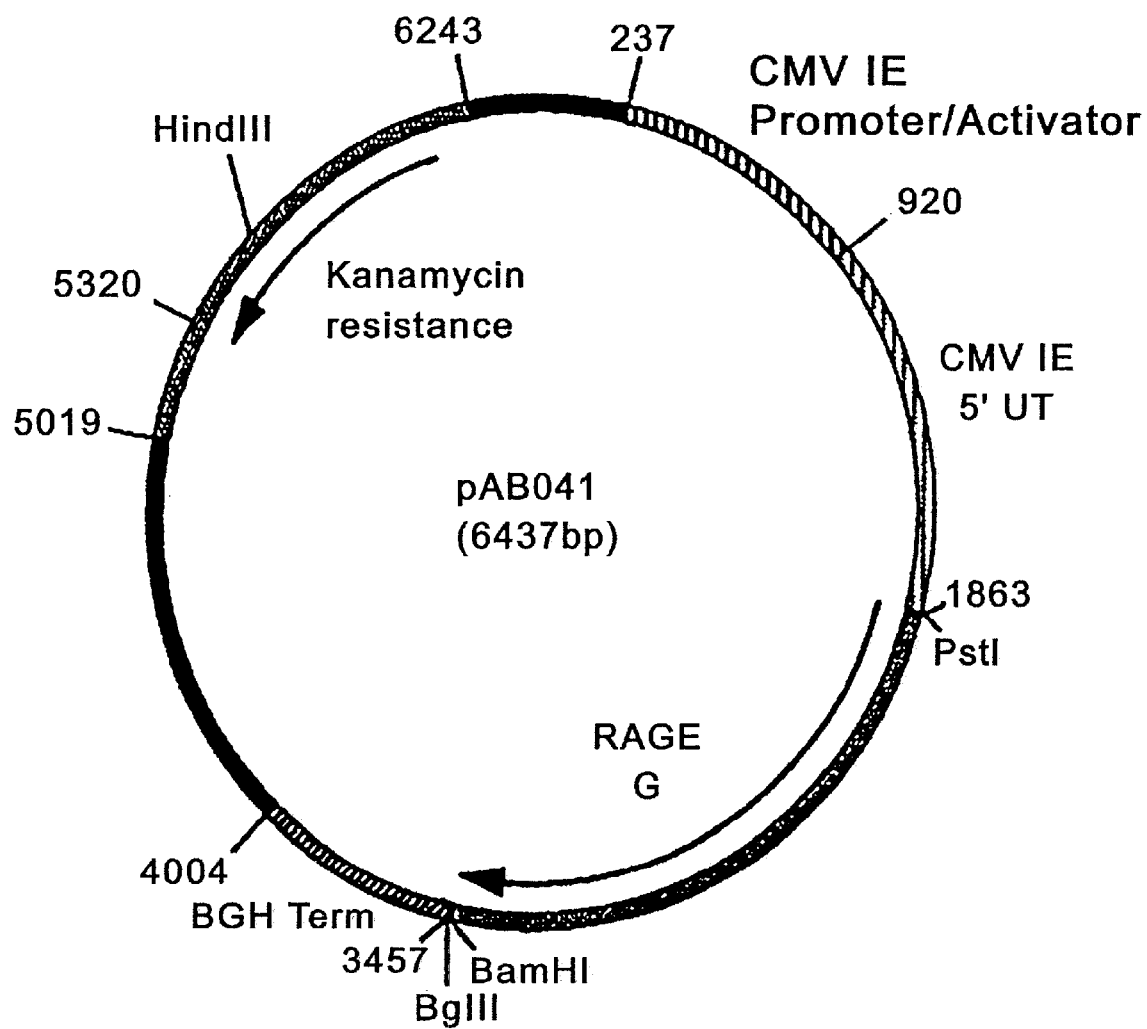
FIG. 10: Plasmid pAB041

An RT-PCR reaction according to the technique of Example 6 was carried out with the rabies virus (ERA strain)

genomic RNA (A. Anilionis et al., Nature, 1981, 294, 275–278), prepared according to the technique of Example 4, and with the following oligonucleotides:
AB011 (33 mer) (SEQ ID No. 17)
5' AAAACTGCAGACATGGTTCCTCAGGCTCTCCTG 3'
AB012 (34 mer) (SEQ ID No. 18)
5' CGCGGATCCTCACAGTCTGGTCTCACCCCCACTC 3'
so as to amplify a 1589 bp fragment containing the gene encoding the rabies virus G glycoprotein. After purification, the RT-PCR product was digested with PstI and BamHI to give a 1578 bp PstI-BamHI fragment. This fragment was ligated with the vector pVR1012 (Example 7), previously digested with PstI and BamHI, to give the plasmid pAB041 (6437 bp) (FIG. 10).

Example 17

Production and Purification of the Plasmids

For the preparation of the plasmids intended for the vaccination of animals, any technique may be used which makes it possible to obtain a suspension of purified plasmids predominantly in the supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (*Molecular Cloning: A Laboratory Manual,* 2nd edition, Cold Spring Harbor Laboratory, Cold Spring Harbor, N.Y., 1989). Reference may also be made to patent applications PCT WO 95/21250 and PCT WO 96/02658 which describe methods for producing, on an industrial scale, plasmids which can be used for vaccination. For the purposes of the manufacture of vaccines (see Example 18), the purified plasmids are resuspended so as to obtain solutions at a high concentration (>2 mg/ml) which are compatible with storage. To do this the plasmids are resuspended either in ultrapure water or in TE buffer (10 mM Tris-HCl; 1 mM EDTA, pH 8.0).

Example 18

Manufacture of the Associated Vaccines

The various plasmids necessary for the manufacture of an associated vaccine are mixed starting with their concentrated solutions (Example 16). The mixtures are prepared such that the final concentration of each plasmid corresponds to the effective dose of each plasmid. The solutions which can be used to adjust the final concentration of the vaccine may be either a 0.9% NaCl solution, or PBS buffer.

Specific formulations, such as liposomes and cationic lipids, may also be used for the manufacture of the vaccines.

Example 19

Vaccination of Dogs

The dogs are vaccinated with doses of 10 µg, 50 µg or 250 µg per plasmid.

The injections can be performed with a needle by the intramuscular route. In this case, the vaccinal doses are administered in volumes of 1 or 2 ml. The injections may be performed with a needle by the intradermal route. In this case, the vaccinal doses are administered in a total volume of 1 ml administered at 10 points of 0.1 ml or at 20 points of 0.05 ml. The intradermal injections are performed after shaving the skin (thoracic flank in general) or at the level of a relatively glabrous anatomical region, for example the inner surface of the thigh. A liquid jet injection apparatus can also be used for the intradermal injections.

What is claimed is:

1. A Canidae vaccine comprising an effective amount to elicit a protective immune response in a Canidae of a plasmid that contains and expresses in a Canidae host cell a nucleic acid molecule having a nucleic acid sequence encoding rabies G, and a pharmaceutically acceptable carrier.

2. The vaccine according to claim 1, wherein expression of the nucleic acid sequence is under the control of a promoter selected from the group consisting of a CMV-IE promoter, a SV40 early promoter, a SV40 late promoter, a Rous sarcoma virus LTR promoter, and a promoter of a cytoskeleton gene.

3. The vaccine according to claim 2, wherein the promoter is a CMV-IE promoter.

4. The vaccine according to claim 1, in a dose volume between 0.1 and 5 ml.

5. The vaccine according to claim 4, in a dose volume between 0.5 and 2 ml.

6. The vaccine according to claim 1, which comprises from 10 ng to 1 mg, of the plasmid.

7. The vaccine according to claim 6, which comprises from 100 ng to 500 µg, of the plasmid.

8. The vaccine according to claim 6, which comprises between 1 µg and 250 µg of the plasmid.

9. A Canidae vaccine comprising an effective amount to elicit a protective immune response in a Canidae of a plasmid that contains and expresses in a Canidae host cell a nucleic acid molecule having a nucleic acid sequence encoding rabies G, and a pharmaceutically acceptable carrier, wherein the plasmid further contains and expresses in vivo in a Canidae host cell a nucleic acid molecule having a nucleic acid sequence from another Canidae pathogen.

10. A method for vaccinating a Canidae comprising administering to said Canidae an effective amount to confer protective immunity in the Canidae of a Canidae vaccine comprising an effective amount to elicit a protective immune response in a Canidae of a plasmid that contains and expresses in a Canidae host cell a nucleic acid molecule having a nucleic acid sequence encoding rabies G, and a pharmaceutically acceptable carrier.

11. A method for vaccinating a Canidae according to claim 10 wherein the plasmid expression of the nucleic acid sequence is under the control of a promoter selected from the group consisting of a CMV-IE promoter, a SV40 early promoter, a SV40 late promoter, a Rous sarcoma virus LTR promoter, and a promoter of a cytoskeleton gene.

12. A method for vaccinating a Canidae according to claim 11 wherein the promoter is a CMV-IE promoter.

13. A method for vaccinating a Canidae according to claim 10 wherein the vaccine is in a dose volume between 0.1 and 5 ml.

14. A method for vaccinating a Canidae according to claim 13 wherein the vaccine is in a dose volume between 0.5 and 2 ml.

15. A method for vaccinating a Canidae according to claim 10 wherein the vaccine comprises from 10 ng to 1 mg, of the plasmid.

16. A method for vaccinating a Canidae according to claim 15 wherein the vaccine comprises from 100 ng to 500 µg, of the plasmid.

17. A method for vaccinating a Canidae according to claim 15 wherein the vaccine comprises between 1 µg and 250 µg of the plasmid.

18. A method for vaccinating a Canidae according to claim 10 wherein the plasmid further contains and expresses in vivo in a Canidae host cell a nucleic acid molecule having a nucleic acid sequence from another Canidae pathogen.

19. A method of vaccinating a Canidae host comprising:

administering to said Canidae a vaccine selected from the group consisting of a live whole vaccine, an inactivated whole vaccine, a subunit vaccine, and a recombinant vaccine; and thereafter, administering a Canidae vaccine comprising an effective amount to elicit a protective immune response in a Canidae of a plasmid that contains and expresses in a Canidae host cell a nucleic acid molecule having a nucleic acid sequence encoding rabies G, and a pharmaceutically acceptable carrier.

20. A kit comprising (i) a Canidae vaccine comprising an effective amount to elicit a protective immune response in a Canidae of a plasmid that contains and expresses in a Canidae host cell a nucleic acid molecule having a nucleic acid sequence encoding rabies G, and a pharmaceutically acceptable carrier, and (ii) a Canidae vaccine selected from the group consisting of a live whole vaccine, an inactivated whole vaccine, a subunit vaccine, and recombinant vaccine.

* * * * *

UNITED STATES PATENT AND TRADEMARK OFFICE
CERTIFICATE OF CORRECTION

PATENT NO.     : 6,586,412 B2  
DATED          : July 1, 2003  
INVENTOR(S)    : Jean-Christophe Audonnet et al.

It is certified that error appears in the above-identified patent and that said Letters Patent is hereby corrected as shown below:

<u>Title page,</u>  
Item [75], Inventors, change "Lyons" to -- Lyon --  
Item [73], Assignee, change "Lyons" to -- Lyon --

Signed and Sealed this

Twenty-eighth Day of October, 2003

JAMES E. ROGAN  
*Director of the United States Patent and Trademark Office*

SEQUENCE LISTING

<160> NUMBER OF SEQ ID NOS: 18

<210> SEQ ID NO 1
<211> LENGTH: 35
<212> TYPE: DNA
<213> ORGANISM: Borrelia burgdorferi

<400> SEQUENCE: 1
aaaactgcag aatgctcccc taccaagaca aggtg                35

<210> SEQ ID NO 2
<211> LENGTH: 37
<212> TYPE: DNA
<213> ORGANISM: Borrelia burgdorferi

<400> SEQUENCE: 2
cgcggatcct taacggttac atgagaatct tatacgg              37

<210> SEQ ID NO 3
<211> LENGTH: 40
<212> TYPE: DNA
<213> ORGANISM: Borrelia burgdorferi

<400> SEQUENCE: 3
ataagaagcg gccgcacatg cacaagggaa tccccaaaag           40

<210> SEQ ID NO 4
<211> LENGTH: 32
<212> TYPE: DNA
<213> ORGANISM: Borrelia burgdorferi

<400> SEQUENCE: 4
cgcggatcca cttcagtgtg atctcacata gg                     32

<210> SEQ ID NO 5
<211> LENGTH: 33
<212> TYPE: DNA
<213> ORGANISM: Borrelia burgdorferi

<400> SEQUENCE: 5
acgcgtcgac atgagtgatg gagcagttca acc                    33

<210> SEQ ID NO 6
<211> LENGTH: 33
<212> TYPE: DNA
<213> ORGANISM: Borrelia burgdorferi

<400> SEQUENCE: 6
cgcggatcct aatataatt ttctaggtgc tag                     33

<210> SEQ ID NO 7
<211> LENGTH: 32
<212> TYPE: DNA
<213> ORGANISM: Borrelia burgdorferi

<400> SEQUENCE: 7
acgcgtcgac atgattgtgc ttacattgtg cc                     32

<210> SEQ ID NO 8
<211> LENGTH: 35
<212> TYPE: DNA
<213> ORGANISM: Borrelia burgdorferi

<400> SEQUENCE: 8
cgcggatcct cagtgaacat gaactttttc aatag                  35

<210> SEQ ID NO 9
<211> LENGTH: 34
<212> TYPE: DNA
<213> ORGANISM: Borrelia burgdorferi

<400> SEQUENCE: 9
aaaactgcag aaatgaagaa aattttgttt ttac                   34

<210> SEQ ID NO 10
<211> LENGTH: 33
<212> TYPE: DNA
<213> ORGANISM: Borrelia burgdorferi

<400> SEQUENCE: 10
cgcggatcct tataccatat gtaataattt ttc                    33

<210> SEQ ID NO 11
<211> LENGTH: 34
<212> TYPE: DNA
<213> ORGANISM: Borrelia burgdorferi

<400> SEQUENCE: 11
aaaactgcag aagtatgttt tcattgtatc tata                   34

```
<210> SEQ ID NO 12
<211> LENGTH: 34
<212> TYPE: DNA
<213> ORGANISM: Borrelia burgdorferi

<400> SEQUENCE: 12
ctagtctaga ttattaaact ttactttcat tttc                                34

<210> SEQ ID NO 13
<211> LENGTH: 34
<212> TYPE: DNA
<213> ORGANISM: Borrelia burgdorferi

<400> SEQUENCE: 13
aaaactgcag aaaatgatta aacttctarr ratc                                34

<210> SEQ ID NO 14
<211> LENGTH: 35
<212> TYPE: DNA
<213> ORGANISM: Borrelia burgdorferi

<400> SEQUENCE: 14
ataagaatgc ggccgcaaag gctaaacatt tgttg                               35

<210> SEQ ID NO 15
<211> LENGTH: 37
<212> TYPE: DNA
<213> ORGANISM: Borrelia burgdorferi

<400> SEQUENCE: 15
acgcgtcgac tatgaaaaaa tatttattgg gaatagg                             37

<210> SEQ ID NO 16
<211> LENGTH: 34
<212> TYPE: DNA
<213> ORGANISM: Borrelia burgdorferi

<400> SEQUENCE: 16
cgcggatccc ttattttaaa gcgttttttaa tttc                               34

<210> SEQ ID NO 17
<211> LENGTH: 33
<212> TYPE: DNA
<213> ORGANISM: Borrelia burgdorferi

<400> SEQUENCE: 17
aaaactgcag agatggttcc tcaggctctc ctg                                 33

<210> SEQ ID NO 18
<211> LENGTH: 34
<212> TYPE: DNA
<213> ORGANISM: Borrelia burgdorferi

<400> SEQUENCE: 18
cgcggatcct cacagtctgg tctcacccc actc                                 34
```